United States Patent [19]

Pawlak

[11] Patent Number: 4,892,817
[45] Date of Patent: Jan. 9, 1990

[54] STABLE PHOSPHATASE SUBSTRATE COMPOSITION

[75] Inventor: Jan W. Pawlak, Oakland, Calif.

[73] Assignee: Biogenex Laboratories, San Ramon, Calif.

[21] Appl. No.: 99,062

[22] Filed: Sep. 21, 1987

[51] Int. Cl.$^4$ ............................ C12Q 1/42; C12Q 1/00
[52] U.S. Cl. ............................................ 435/21; 435/4
[58] Field of Search ..................... 435/4, 21, 188, 195, 435/196

[56] References Cited

U.S. PATENT DOCUMENTS

| | | | |
|---|---|---|---|
| 4,284,948 | 11/1988 | Scott et al. | 435/68 |
| 4,555,484 | 11/1985 | La Rossa et al. | 435/21 |
| 4,713,327 | 12/1987 | Findlay et al. | 435/17 |
| 4,748,115 | 5/1988 | Steaffens | 435/21 |
| 4,782,017 | 11/1988 | Frickey et al. | 435/21 |

Primary Examiner—David M. Naff
Attorney, Agent, or Firm—Richard L. Neeley

[57] ABSTRACT

A stabilized phosphatase substrate composition is provided comprising an indoxl phosphate, a tetrazolium salt, and a water-soluble ferricyanide/ferrocyanide salt. When present as a solution, the composition also contains a buffer that produces a pH in a range of from about 8 to about 11.

18 Claims, No Drawings

STABLE PHOSPHATASE SUBSTRATE COMPOSITION

FIELD OF THE INVENTION

The present invention is directed to phosphatase substrates and their use in a variety of chemical and biochemical assays involving phosphatase.

BACKGROUND OF THE INVENTION

Enzyme activity that can liberate phosphoric acid from certain precursor compounds has been known since the beginning of this century. These enzymes, known as phosphatases, have a ubiquitous distribution in biological systems, although relatively little is known about their biological function.

Recently, phosphatases have been used as detectable labels in a number of analytical assays based on the use of enzymes as labels for a member of a specific binding pair. These assays rely on the recognition between members of the binding pair and the detection of a label on one member of the binding pair to indicate the presence of the other member. Examples of binding pair members include antibodies (including binding fragments) and antigens, nucleic acid probes (both DNA and RNA) and their conjugates, carbohydrates and lectins, and hormones and their receptor proteins.

Use of a phosphatase in either a histological staining process or as a detectable label requires a substrate for the phosphatase that undergoes a detectable change as a result of the action of the enzyme on the substrate. The general types of substrates known to exist for phosphatases include esters and amides of phosphoric acid. Of these, mono- and di-esters of alcohols and phenols have been utilized for the most part. In general, the nature of the organic radical does not affect the specificity of the reaction. Phosphatases also hydrolize the S-P bond of thioesters. A number of phosphatase substrate types are set forth in the following table.

TABLE
Phosphatase Substrate Types*

| | | |
|---|---|---|
| 1. | Alk—O*P | Phosphate esters of alkyl alcohols (Alk = alkyl grouping) |
| 2. | Ar—O*P | Aryl phosphate esters (Ar = aryl grouping) |
| 3. | Ar—Alk—O*P | Arylalkyl phosphate esters |
| 4. | C═C—O*P | Enol phosphates (e.g., phosphopyruvic acid) |
| 5. | R—CO—O*P | Acyl phosphates (e.g., acetyl phosphate) |
| 6. | (ArO)$_2$*P | Diaryl phosphates |
| 7. | P*OP | Inorganic pyrophosphate |
| 8. | (Ar,Alk)P*OP | Organic pyrophosphate |
| 9. | Ar —N*P | Phosphamide (Ar = aryl grouping, creatine, or arginine) |
| 10. | (Ar,Alk)S*P | Thioesters |

*Location of bond being cleaved.

Examples of specific techniques used in dyeing of tissue samples include the metal-salt phosphatase technique that depends in its original version upon the enzymatic release of phosphate ions that are precipitated as insoluble calcium phosphate. The calcium phosphate is then visualized, for example by conversion to cobalt sulfide, conversion to silver phosphate followed by exposure to light, reaction with either sodium alizarin sulfonate or phthalocyanine dyes to form a calcium lake, or reaction with pentahydroxyflavone to form a fluorescent lake.

Another dyeing technique that also releases a visible component for use with enzyme labels in analytical techniques is the azo-dye technique. This technique relies upon the coupling of various components (under either alkaline or acid conditions) after enzymatic hydrolysis of phosphate esters of the coupling components. The released coupling agent couples with a diazonium component to form a highly colored azo dye. In a modification of this technique, known as a postcoupling procedure, incubation with enzyme is carried out in the absence of a diazonium salt, which is added later. General configuration of typical phosphate esters used in the azo-dye method are shown in the formulas below:

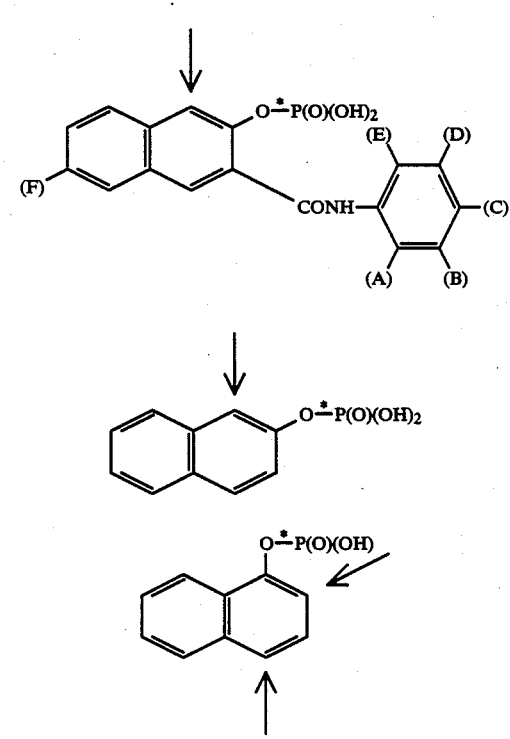

In these formulas, (A) through (F) indicate the location of various substituents, which can be either electropositive and/or electronegative. The asterisk indicates the point of hydrolysis upon action of phosphase, and the arrow indicates the coupling position in the naphthol to the diazonium salt component (the broken arrow indicates a less reactive coupling position). Commonly used diazonium salts are shown in the following formulas, in which (+) represents an electropositive substituent, (−) represents an electronegative substituent, and (A) through (J) indicate the position of various groupings in known compounds that can be either (+) or (−).

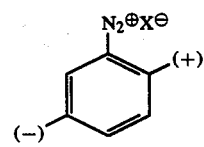

technique is shown in the reaction scheme set forth below.

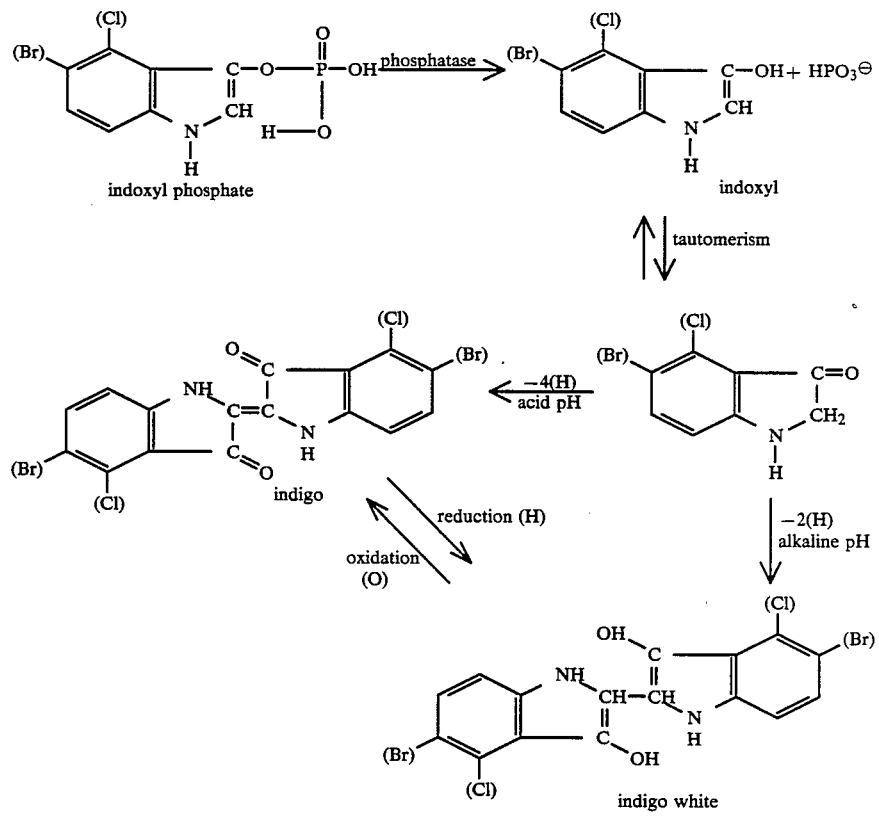

A fourth technique is the indoxyl phosphate/tetrazolium salt method in which at an alkaline pH the production of indigo decreases and the production of colorless dehydroindigo increases. The hydrogen released by the formation of indigo or dehydroindigo reduces colorless soluble tetrazolium salt to colored insoluble diformazan at the enzyme site as shown in the following exemplary scheme.

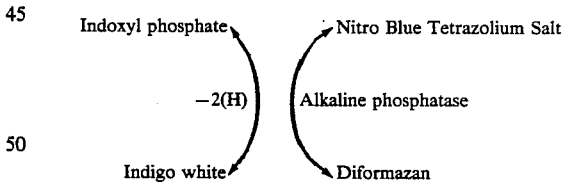

There are a number of problems associated with available phosphatase substrates used in the methods set forth above. For example, the most widely used diazonium salts in the azo-dye method are arylamine diazonium chlorides and analogous simple salts. These compounds are unstable in solution and require refrigeration in dry form for storage. Even at low temperature, slow decomposition occurs over a period of time. Commercial techniques of stabilization include the use of aluminum, magnesium, and zinc sulfates; magnesium oxide; magnesium bicarbonate; and disodium naphthalene-1,6-disulfonate. Even though small quantities of diazonium salts are used, the metallic and other stabilizers exert a marked inhibitory affect upon phosphatases and other enzymes that may be present (such as oxidases). Additionally, diffusion artifacts occur when there is time for

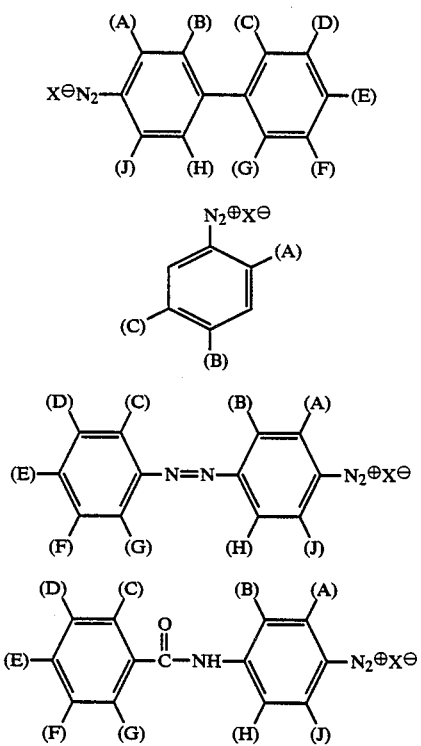

An additional technique of visualization is based on the oxidation of indoxyl substrates, such as 3-indoxyl phosphate, to indigo dyes. The principle of the indoxyl soluble components released from an enzyme reaction to diffuse away from the reaction site before precipitation and/or color formation occurs. Accordingly, there remains a need for improved phosphatase substrates that are stable without the inhibiting stabilizers used with various substrates now available and which will be insoluble and highly colored immediately upon release without requiring the occurrence of other reactions after the phosphatase reaction is completed.

SUMMARY OF THE INVENTION

The present invention accordingly provides a stabilized alkaline phosphatase substrate composition that is both stable and active at the pH of maximum phosphatase activity (above pH 9). Furthermore, the composition is stable through long term storage and contains no stabilizers that interfere with enzyme activity. The composition comprises an indoxyl phosphate compound, an ferricyanide/ferrocyanide stabilizing agent, and a tetrazolium salt.

DESCRIPTION OF SPECIFIC EMBODIMENTS

Stabilized phosphatase substrate compositions are provided comprising an indoxyl phosphate, a tetrazolium salt, and a ferricyanide/ferrocyanide salt. The composition generally also contains a buffer capable of producing a pH in a range of from about 8–11 in the presence of the first three components in an aqueous solution. Such stabilized phosphatase substrate compositions show long shelf life and can readily be used in known techniques of the indoxyl phosphate type in which a phosphatase enzyme is used as a detectable label or in histological staining techniques.

The first component present in the phosphatase substrate composition is an indoxyl phosphate. The indoxyl phosphate can be any indoxyl phosphate derivative capable of being hydrolized by phosphatase to the corresponding indoxy compound. Since phosphatases are quite liberal in recognizing and cleaving phosphate bonds despite the structure of the alkyl or aryl group attached to the oxygen of the phosphate bond, there are no known limitations on the substituents that are present on the phenyl ring that forms part of the indole ring system. However, relatively small substituents smaller in size than a phenyl group and preferably containing four or fewer carbons in the hydrocarbyl portion thereof are preferred. Typical substituents and functional groups can be present on the hydrocarbyl portion, particularly functional groups and/or substituents that render the entire substituent electronegative, such as halogen and various oxygen-containing functional groups. Non-hydrocarbyl substituents directly attached to the phenyl ring are preferably nitro, hydrocarbyloxy, acyl (carboxylic acid residues), and halogen. Halogen substituents are most preferred. No substitution is possible on position 2 of the indole ring as this position must be free to participate in the coupling reaction shown above for the formation of indigo. Hydrocarbyl substituents are permitted on the nitrogen of the indole ring system in a similar manner to that described above for the phenyl ring, but hydrogen is preferred. Particularly preferred compounds are 3-indoxyl phosphate and 5-bromo-4-chloro-3-indoxyl phosphate.

The tetrazolium salt is an organic salt in which the organic portion contains one or two tetrazole rings, generally with aryl (especially phenyl or substituted phenyl) substituents at various positions, particularly the 2, 3, and 5 positions. Tetrazolium salts with two tetrazole rings are typically coupled so as to provide a diphenyl group (theoretically using two of the previously mentioned phenyl substituents) with the tetrazole rings in the two para positions. The tetrazolium-containing organic component provides all or part of the positive charge of the salt with the negative charge being provided by an organic or inorganic negative ion, typically an inorganic halide ion. Exemplary tetrazolium compounds include the following: Nitrotetrazolium Violet; p-Nitro Blue Tetrazolium Chloride; m-Nitro Blue Tetrazolium Chloride; [3-(4,5-Dimethylthiazol-2-yl)-2,5-diphenyl]tetrazolium Bromide (MTT), Iodo Nitro Tetrazolium Violet Chloride, 2,3,5-Triphenyl Tetrazolium Chloride; Distyryl Nitro Blue Tetrazolium Chloride; p-Anisyl Blue Tetrazolium Chloride; Tetranitro Blue Tetrazolium Chloride; 2,5-diphenyl-3-[α-naphthyl]-tetrazolium chloride; 2,2',5,5'-Tetraphenyl-3,3'(p- diphenylene)-ditetrazolium chloride; m-Nitro Neotetrazolium Chloride; 2-(2'-Benzothiazolyl)-5-styryl-3-(4'-phthalhydrazidyl)-tetrazolium chloride; 2,2'-di-p-nitrophenyl-5,5'-di-p-thiocarbamyl-phenyl-3,3'[3,3'-dimethoxy-4,4'-biphenylene]ditetrazolium chloride; o-Tolyl Tetrazolium Red; p-Tolyl Tetrazolium Red; Piperonyl Tetrazolium Blue; p-Anisyl-p-Nitro Blue Tetrazolium Chloride; and Veratryl Tetrazolium Blue. Of these, Nitrotetrazolium Violet, p-Nitro Blue Tetrazolium, MTT, and Iodonitro-tetrazolium salts are preferred.

The indoxyl phosphate and tetrazolium salt components of the composition are themselves well known. However, the stability of such compositions were poor which resulted in decreasing sensitivity and increasing background reactions in the indoxyl phosphate/tetrazolium reaction scheme previously discussed above. However, the present invention provides that the indoxyl phosphate and tetrazolium salt are provided in combination with a water-soluble ferricyanide/ferrocyanide salt. Since the composition is intended for use with an alkaline phosphatase, a buffer capable of producing a pH in a range of from about 8 to 11 is also generally present.

The stabilizer requirement is quite specific. Other $Fe^{3+}/Fe^{2+}$ salts, as well as other metal salt combinations known to stabilize other compositions, have been proven not suitable for the present invention. For example, a ferric chloride/ferrous chloride solution did not prove capable of stabilizing the indoxyl phosphate/tetrazolium salt compositions described herein. Particularly preferred are alkali metal ferricyanide and ferrocyanide salts, especially potassium salts. In the mixture, the molar ratio of $Fe^{3+}$ to $Fe^{2+}$ can range from about 1:1 to about 20:1, preferably from about 3:1 to about 12:1, and most preferably from about 7:1 to about 10:1. Compositions containing a desired ratio of ferric to ferrous ions can readily be prepared by dissolving the calculated amounts of the respective salts in water.

The composition also generally contains a buffer that provides good buffering capabilities over the pH range from about 8 to about 11, preferably about 9–10. Among buffers designed for use in this range, organic alcohols with a primary amino substituent are preferred, particularly organic alcohols having from 2–6 carbon atoms, 1 or 2 primary amino groups, and 2 or fewer hydroxyl groups. The buffer known as AMPD (2-amino-2-methyl-1,3-propanediol) is a preferred buffer, as is 2-amino-2-methylpropanol.

Although the components of the compositions can be prepared in dry form for dilution (for example, with an aqueous buffer as described above), aqueous compositions are preferred. When prepared as an aqueous composition, the final composition of the invention normally contains an indoxyl phosphate in a concentration of from about 0.05 to about 2 mg/ml, preferably from about 0.1 to about 1 mg/ml, and most preferably from about 0.25 to about 0.75 mg/ml; a tetrazolium salt in a concentration of from about 0.1 to about 1 mg/ml and more preferably from about 0.2 to about 0.75 mg/ml; an $Fe^{3+}/Fe^{2+}$ cyanide salt (total iron concentration) in a concentration of from about 0.05 to about 2 mM and more preferably from about 0.25 to about 1.25 mM; and a buffer in a concentration of from about 20 to about 250 mM, and more preferably from about 50 to about 125 mM. It should be noted that each of the limits set forth can be selected independently for use with other expressed limits to provide ranges of intermediate desirability. For example, a normal upper limit can be combined with a preferred lower limit to express a range of intermediate preference.

The aqueous composition is typically prepared from distilled water, but other components can be present, including ethanol or dimethylformamide. These two organic solvents (miscible with water) can be used to prepare mixed organic/water-containing aqueous solutions in which the organic solvent comprises up to 5% (v/v) of the solvent.

Other components can be present in the composition, such as bactericides to limit bacterial degradation; for example, $NaN_3$ at 0.05 to 0.1% (w/v).

Particularly, preferred compositions are those in which the indoxyl phosphate is 3-indoxyl phosphate or 5-bromo-4-chloro-3-phosphate; the tetrazolium salt is Nitrotetrazolium Violet, p-Nitro Blue Tetrazolium Chloride, m-Nitro Blue Tetrazolium Chloride, [3-(4,5-Dimethylthiazol-2-yl)-2,5-diphenyl]tetrazolium Bromide, Iodo Nitro Tetrazolium Violet Chloride, 2,3,5-Triphenyl Tetrazolium Chloride, Distyryl Nitro Blue Tetrazolium Chloride, p-Anisyl Blue Tetrazolium Chloride, Tetranitro Blue Tetrazolium Chloride, 2,5-diphenyl-3-[α-naphthyl]-tetrazolium chloride, 2,2',5,5'Tetraphenyl-3,3'(p-diphenylene)-ditetrazolium chloride, m-Nitro Neotetrazolium Chloride, 2-(2'-Benzothiazolyl)-5-styryl-3-(4'-phthalhydrazidyl)-tetrazolium chloride, 2,2'-di-p-nitrophenyl-5,5'-di-p-thiocarbamylphenyl-3,3+[3,3'-dimethoxy-4,4'-biphenylene]ditetrazolium chloride, o-Tolyl Tetrazolium Red, p-Tolyl Tetrazolium Red, Piperonyl Tetrazolium Blue, p-Anisyl-p-Nitro Blue Tetrazolium Chloride, or Veratryl Tetrazolium Blue; the soluble iron salt is a mixture of ferricyanide and ferrocyanide alkali metal salts; and the buffering agent is an organic alcohol with a primary amino substituent, especially AMPD. Aqueous solutions buffered in the range from pH 9-10 are especially preferred.

Because of the adverse affect that various metal ions previously used as stabilizers have had on phosphatase, preferred compositions contain no metal ions other than potassium or sodium. The compositions also preferably contain no multivalent ions other than ferricyanide and ferrocyanide ions.

Additional advantages are obtained by preparing the compositions in polyalkylene containers (such as polyethylene, polypropylene, and the like), especially polypropylene containers.

Compositions of the invention can be prepared by dissolving the indoxyl phosphate at a concentration twice the desired final concentration in a solution of the buffer containing antimicrobial agents. A solution of the $Fe^{3+}/Fe^{2+}$ salts is then added followed by the tetrazolium salt solution (which can be in water, an organic solvent such as dimethylformamide, or a mixed water/organic solvent as is necessary for solubility), both additional solutions being added with mixing. Sufficient deionized water is then added to provide the desired concentration. Most desirably these mixing reactions are carried out in polypropylene containers, after which the container of solution is tightly closed and stored in darkness at room temperature (about 18°-25° C.) for about 24 hours (normally at least 12 but less than 48 hours). The solution is then filtered to remove insoluble material prior to storage. A filter having pore diameters of about 0.45 μm provides satisfactory results.

The stabilized compositions of the invention can be used in any method in which indoxyl phosphate/tetrazolium compositions have previously been used. A number of exemplary techniques include dipstick and flow through immunochemical devices, Southern blot, Northern blot, and Western blot analyses; and immunohistochemical staining.

The invention now being generally described, the same will be better understood by reference to the following examples which are provided for purposes of illustration and are not to be considered limiting of the invention unless so specified.

EXAMPLES

Abbreviations

BCIP=5-bromo-4-chloro-3-indoxyl phosphate (American Research Products Company, Solon, Ohio; cat. #P0885)

3-IP=3-indoxyl phosphate (disodium salt; Sigma cat. #J-5505)

AMPD=2-Amino-2-methyl-1,3-propanediol (Sigma cat. #A-9754)

NTV=Nitrotetrazolium Violet (Polysciences, Inc., Harrington, PA 18976; cat. #4126)

NBT=p-Nitro Blue Tetrazolium Chloride (p-NBT; United States Biochemical Corporation, Cleveland, Ohio; cat. #19535)

m-NBT=m-Nitro Blue Tetrazolium Chloride (USBC; cat. #19550)

MTT=[3-(4,5-Dimethylthiazol-2-yl)-2,5-diphenyl]tetrazolium Bromide (Sigma cat. #M-2128)

INT=Iodo Nitro Tetrazolium Violet Chloride ((USBC; cat. #18809)

TPT=2,3,5-Triphenyl Tetrazolium Chloride (TTC, TR, Tetrazolium Red; Sigma cat. #T-8877)

DS-NBT=Distyryl Nitro Blue Tetrazolium Chloride (Polysciences, Inc.; cat. #3441)

pABT=p-Anisyl Blue Tetrazolium Chloride (USBC; cat. #11325)

TNBT=Tetranitro Blue Tetrazolium Chloride (USBC; cat. #22130)

TV=2,5-diphenyl-3-[α-naphthyl]-tetrazolium chloride (Tetrazolium Violet; Sigma cat. #T-0138)

NT=2,2',5,5'-Tetraphenyl-3,3'(p-diphenylene)-ditetrazolium chloride (Neotetrazolium Chloride; Sigma cat. #N-2251)

m-NNT=m-Nitro Neotetrazolium Chloride (USBC; cat. #19575)

BSPT=2-(2'-Benzothiazolyl)-5-styryl-3-(4'-phthalhydrazidyl)-tetrazolium chloride (Sigma cat. #B-8131)

TC-NBT=2,2'-di-p-nitrophenyl-5,5'-di-p-thiocarbamylphenyl-3,3'[3,3'-dimethoxy-4,4'-biphenylene]- ditetrazolium chloride (Thiocarbamyl Nitro Blue Tetrazolium Chloride; Sigma cat. #T-7002)
o-TTR=o-Tolyl Tetrazolium Red (USBC; cat. #22440)
pTTR=p-Tolyl Tetrazolium Red (USBC; cat. #22445)
PTB=Piperonyl Tetrazolium Blue (USBC; cat. #20420)
pApNBT=p-Anisyl-p-Nitro Blue Tetrazolium Chloride (USBC; cat. #11335)
VTB=Veratryl Tetrazolium Blue (USBC; cat. #23295)

Preparation of Stabilized Indoxyl Phosphate/Tetrazolium Salt Compositions

An indoxyl phosphate (either 3-indoxyl phosphate or 5-bromo-4-chloro-3-indoxyl phosphate) was dissolved at a concentration twice that desired for the final solution in 0.2 M buffer. The various experiments set forth below identify the specific indoxyl phosphate used and its concentration as well as the buffer used and its exact pH. Deionized water, a solution of potassium ferricyanide and potassium ferrocyanide, and a tetrazolium salt solution were added sequentially to the indoxyl phosphate solution with stirring to provide the final concentrations and individual components set forth in the examples below.

All of the preceding steps were carried out in polypropylene containers, which were closed tightly and stored in darkness at room temperature for about 24 hours. After storage, the contents were filtered through 0.20 μm Durapore filters (Millipore). Aliquots were then stored in polypropylene vials protected from light.

Stability and Activity of Specific Compositions of the Invention and Comparison Compositions A primary feature of the present invention is the provision of a stable phosphatase substrate solution. The stability of the present solutions is exemplified by the fact that the solutions can be stored at 37° C. for periods of one week, or longer, without impairment of sensitivity or an increase in background reaction products. Measurement of storage stability at 37° C. for one week is an accepted measure used to demonstrate the stability of a composition for one year at 4° C. See, for example, Kirkwood, *Biometrics* (1977) 33:736-742, and Tydeman and Kirkwood, *J. Biol. Stand.* (1984) 12:195-206.

The stability of the preparation was assessed by incubating 10 μl of diluted alkaline phosphatase with 50 μl of the substrate formulation and determining the minimum enzyme concentration that caused a detectable color change. The formulation under study was considered stable if it showed the same activity at 0, 3, and 7 days of incubation at 37° C.

To determine the reactivity of a phosphatase substrate composition, a series of dilutions of alkaline phosphatase prepared in phosphate buffered saline containing 1% BSA, 0.4% Tween-20, and 0.1% $NaN_3$. For example, a solution of alkaline phosphatase at 5 mg/ml with a specific activity of 1500 U/mg was serially diluted five times in a series from 1:250 to 1:781,250 in the buffer just described. One unit of phosphatase activity is equivalent to 1 μm of p-nitrophenyl phosphate hydrolyzed per minute at 25° C. in 0.5M diethanolamine buffer at pH 9.5.

To carry out the reaction, 10 μl of the diluted alkaline phosphatase solutions were added to alternate wells of a polyvinyl microtitre plate followed by addition of 50 μl of phosphatase substrate formulation to each well. When color distinct from that of adjacent substrate color (a well containing no added enzyme) was detected, the time of reaction was recorded for each of the test solutions. For example, the following values were observed for substrate formulation #7 from Table 1 below: 1 sec at 6250 dilution, 7 sec at 31,250 dilution, 50 sec at 156,250 dilution, and 77 sec at 781,250 dilution. In a similar assay using substrate #1 from Table 1 (a comparative test without the ferricyanide/ferrocyanide stabilizer), the results were as follows: 5 sec at 250 dilution, 9 sec at 1,250 dilution, 20 sec at 6,250 dilution, 31 sec at 31,250 dilution, and 100 sec at 156,250 dilution. The log of reaction time versus log of dilution was then plotted; data points were fit to a linear curve by least squares analysis. Then the dilution of the enzyme for a 1 second color development was read from the curve to produce a numerical indication of substrate sensitivity. Concordantly, the enzyme concentration necessary to obtain visible color development in 60 sec was read from the curve to provide an estimate of turnover rate of the substrate preparation.

Results of the test are shown in the following tables. Table 1 shows the formulations, with formulations 1 and 2 being comparative formulations in common use in the prior art (no ferricyanide/ferrocyanide stabilizing salts). Table 2 shows the effects of various buffers and stabilizing metal salts on indoxyl phosphate/tetrazolium compositions. The buffer AMPD provided very good to excellent effects on stability and reaction rates, while other buffers showed varying effects. Of the stabilizing metal salts, only the ferricyanide/ferrocyanide combination provided excellent stabilization in general. A broad spectrum of protection appears to be specific for the ferricyanide/ferrocyanide combination, since a ferric chloride/ferrous chloride mixture provided poor results (not shown).

The sensitivity and turnover rate of the various alkaline phosphatase substrates of the invention were shown to be comparable to or greater than the comparative compositions (#1 and #2), indicating that the stabilizers did not adversly affect sensitivity or turnover rate (Table 3).

TABLE 1

Examples of Alkaline Phosphatase Substrates Based on Indoxyl Phosphate and Tetrazolium Derivatives

| Substrate Designation | Indoxyl Phosphate Component | | | $Fe^{2+}/Fe^{3+}$ Stabilizer, μl/ml[a] | Tetrazolium Salt Component | | | |
|---|---|---|---|---|---|---|---|---|
| | 3-IP, mg/ml | BCIP, mg/ml | pH of 0.1 M AMPD buffer | | Code | mg/ml | DMF | DMF/$H_2O$ |
| #1 | — | 1.0 | 10.0 | — | — | — | — | — |
| #2 | 1.0 | — | 10.0 | — | — | — | — | — |
| #3 | — | 0.5 | 10.0 | 50 | NBT | 0.50 | — | + |
| #4 | 0.5 | — | 9.0 | 25 | MTT | 0.20 | + | — |
| #5 | — | 0.5 | 10.0 | 25 | pApNBT | 0.25 | + | — |
| #6 | — | 0.5 | 10.0 | 25 | DS-NBT | 0.25 | + | — |
| #7 | 1.0 | — | 10.0 | 25 | NTV | 0.25 | + | — |

TABLE 1-continued

Examples of Alkaline Phosphatase Substrates
Based on Indoxyl Phosphate and Tetrazolium Derivatives

| Substrate Designation | Indoxyl Phosphate Component | | | $Fe^{2+}/Fe^{3+}$ Stabilizer, $\mu l/ml^{(a)}$ | Tetrazolium Salt Component | | | |
|---|---|---|---|---|---|---|---|---|
| | 3-IP, mg/ml | BCIP, mg/ml | pH of 0.1 M AMPD buffer | | Code | mg/ml | DMF | $DMF/H_2O$ |
| #8 | — | 0.5 | — | 10 | INT | 0.35 | + | — |

$^{(a)}Fe^{2+}/Fe^{3+}$ Stabilizer: 7.1 mM potassium ferricyanide ($K_3Fe(CN)_6$; Sigma cat. #P-8131) and 2.4 mM potassium ferrocyanide ($K_4Fe(CN)_6\cdot 3H_2O$; Sigma cat. #P-9387) in deionized water
$^{(b)}DMF:H_2O = 1:1$ (v/v)

TABLE 2

Alkaline Phosphatase Substrates Based on
Indoxyl Phosphate and Tetrazolium Derivatives.

A. Buffers tested for stabilizing effect and conversion rate:

| Buffer System | Stability$^{(a)}$ | Rate$^{(b)}$ |
|---|---|---|
| 0.1 M diethanolamine, pH 8.0 | Poor/Moderate | Slow/Moderate |
| 0.1 M diethanolamine, pH 9.0 | Poor | Fast |
| 0.1 M diethanolamine, pH 10.0 | Very Poor | Very Fast |
| 0.1 M glycine, pH 8.3 | Moderate | Moderate/Fast |
| 0.1 M glycine, pH 9.0 | Poor | Fast |
| 0.1 M bicine, pH 8.3 | Poor | Moderate/Slow |
| 0.1 M bicine, pH 9.0 | Very Poor | Moderate |
| 0.1 M DIPSO, pH 10.0 | Very Poor | Slow/Moderate |
| 0.1 M CAPS, pH 10.5 | Very Poor | Slow/Moderate |
| 0.1 M AMPD, pH 9.0 | V. Good-Excellent | V. Fast-Extr. Fast |
| 0.1 M AMPD, pH 10.0 | V. Good-Excellent | V. Fast-Extr. Fast |
| 0.1 M Tris, pH 9.0 | Moderate/Good | Moderate/Slow |
| 0.1 M Tris, pH 10.0 | Poor/Moderate | Moderate |

Key to terminology on stability:
Very Poor: Inactive within 12 hrs at room temperature
Poor: Inactive after 24 hrs at room temperature
Moderate: Stable up to 3 days at room temperature
Good: Stable for 1 week at room temperature
Very Good: Stable for 1 week at 37° C.
Excellent: Stable for more than 2 weeks at 37° C.

Key to abbreviations:
DIPSO = 3-(dihydroethyl)amino-2-hydroxy-propane sulfonic acid; Sigma cat. #D-8151
CAPS = 3-(cyclohexylamino)-1-propanesulfonic acid; Sigma cat. #C-2632
Tris = Tris(hydroxymethyl)aminomethane; Sigma cat. #T-1503
Bicine = N,N—bis(2-hydroxyethyl)glycine: Sigma cat. #B-3876

B. Stabilizing metal salts tested for stabilizing effect and conversion rates:

| Stabilizing Metal Salts | Results |
|---|---|
| $K_3[Fe(CN)_6]/K_4[Fe(CN)_6]$ | Excellent stabilization in general |
| $CoCl_2$, $CoCl_2/CoF_3$ | Good stabilization in few cases |
| $KMnO_4/MnO_2$ | Moderate stabilization in few cases |
| $CuSO_4$, $CuCl/CuCl_2$ | Poor stabilization in most cases |
| $NiSO_4$ | Poor stabilization in general |

TABLE 3

Sensitivity and Turnover Rate
of Alkaline Phosphatase Substrates

| Designation* | (Sensitivity) × (Turnover Rate) |
|---|---|
| 3-IP/NTV(#7) | $8.9 \times 10^9$ |
| BCIP/INT(#8) | $5.0 \times 10^8$ |
| BCIP/NBT(#3) | $1.0 \times 10^8$ |
| BCIP(#1) | $8.7 \times 10^7$ |
| 3-IP(#2) | $3.7 \times 10^7$ |
| 3-IP/MTT(#4) | $2.5 \times 10^7$ |
| BCIP/pApNBT(#5) | $9.5 \times 10^6$ |
| BCIP/DS-NBT(#6) | $4.4 \times 10^6$ |

*From TABLE 1

All publications mentioned in this specification are indicative of the level of skill of those skilled in the art to which this invention pertains. All publications are herein incorporated by reference to the same extent as if each individual publication was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A stabilized phosphatase substrate composition, comprising:
    (a) an indoxyl phosphate;
    (b) a tetrazolium salt; and
    (c) a water-soluble ferricyanide/ferrocyanide salt, comprising a mixture of ferricyanide and ferrocyanide alkali metal salts having a molar ratio of $Fe^{3+}$ to $Fe^{2+}$ of 1:1 to 20:1.

2. The composition of claim 1, wherein components (a), (b), and (c) are in a buffered aqueous solution at a pH in a range of from about 8 to about 11.

3. The composition of claim 1, wherein said indoxyl phosphate is 3-indoxyl phosphate or 5-bromo-4-chloro-3-indoxyl phosphate.

4. The composition of claim 1, wherein said tetrazolium salt is Nitrotetrazolium Violet, p-Nitro Blue Tetrazolium Chloride, m-Nitro Blue Tetrazolium Chloride, [3-(4,5-Dimethylthiazol-2-yl)-2,5-diphenyl]tetrazolium Bromide, Iodo Nitro Tetrazolium Violet Chloride, 2,3,5-Triphenyl Tetrazolium Chloride, Distyryl Nitro Blue Tetrazolium Chloride, p-Anisyl Blue Tetrazolium Chloride, Tetranitro Blue Tetrazolium Chloride, 2,5-diphenyl-3-[α-naphthyl]-tetrazolium chloride, 2,2′,5,5′-Tetraphenyl-3,3′(p-diphenylene)-ditetrazolium chloride, m-Nitro Neotetrazolium Chloride, 2-(2′-Benzothiazolyl)-5-styryl-3-(4′-phthalhydrazidyl)-tetrazolium chloride, 2,2′-di-p-nitrophenyl-5,5′-di-p-thiocarbamylphenyl-3,3′[3,3′-dimethoxy-4,4′-biphenylene]ditetrazolium chloride, o-Tolyl Tetrazolium Red, p-Tolyl Tetrazolium Red, Piperonyl Tetrazolium Blue, p-Anisyl-p-Nitro Blue Tetrazolium Chloride, or Veratryl Tetrazolium Blue.

5. The composition of claim 1, wherein said mixture comprises potassium ferricyanide and potassium ferrocyanide.

6. The composition of claim 1, wherein said ratio is about 8.

7. The composition of claim 1, wherein said pH is from about 9 to 10.

8. The composition of claim 1, wherein said buffer comprises an organic alcohol with a primary amino substituent.

9. The composition of claim 8, wherein said alcohol has 2 to 6 carbon atoms, 1 or 2 primary amino groups, and 2 or fewer hydroxyl groups.

10. The composition of claim 9, wherein said buffer comprises 2-amino-2-methyl-1,3-propanediol.

11. The composition of claim 2, wherein said indoxyl phosphate is present in a concentration of from 0.05 to 2 mg/ml, said tetrazolium salt is present in a concentration of from 0.1 to 1 mg/ml, and said ferricyanide/ferrocyanide salt is present in a concentration of from 0.05 to 2 mM.

12. The composition of claim 11, wherein said buffer is present in a concentration of from 20 to 250 mM.

13. The composition of claim 11, wherein said indoxyl phosphate is 3-indoxyl phosphate or 5-bromo-4-chloro-3-indoxyl phosphate; said tetrazolium salt is Nitrotetrazolium Violet, p-Nitro Blue Tetrazolium Chloride, m-Nitro Blue Tetrazolium Chloride, [3-(4,5-Dimethylthiazol-2-yl)-2,5-diphenyl]tetrazolium Bromide, Iodo Nitro Tetrazolium Violet Chloride, 2,3,5-Triphenyl Tetrazolium Chloride, Distyryl Nitro Blue Tetrazolium Chloride, p-Anisyl Blue Tetrazolium Chloride, Tetranitro Blue Tetrazolium Chloride, 2,5-diphenyl-3-[α-naphthyl]tetrazolium chloride, 2,2',5,5'-Tetraphenyl-3,3'(p-diphenylene)-ditetrazolium chloride, m-Nitro Neotetrazolium Chloride, 2-(2'-Benzothiazolyl)-5-styryl-3-(4'-phthalhydrazidyl)-tetrazolium chloride, 2,2'-di- p-nitrophenyl-5,5=-di-p-thiocarbamyl-phenyl-3,3'[3,3'-dimethoxy-4,4'-biphenylene]ditetrazolium chloride, o-Tolyl Tetrazolium Red, p-Tolyl Tetrazolium Red, Piperonyl Tetrazolium Blue, p-Anisyl-p-Nitro Blue Tetrazolium Chloride, or Veratryl Tetrazolium Blue; and said ferricyanide/ferrocyanide salt is a mixture of an alkali metal ferricyanide and an alkali metal ferrocyanide.

14. The composition of claim 13, wherein said buffer comprises an organic alcohol with a primary amino substituent and said pH is from about 9 to 10.

15. The composition of claim 14, wherein said composition contains no metal ions other than potassium or sodium.

16. The composition of claim 14, wherein said composition contains no multivalent ions other than ferricyanide and ferrocyanide ions.

17. The composition of claim 14, wherein said composition is in a polypropylene container.

18. The composition of claim 1, wherein said composition is in a polyalkylene container.

* * * * *